(12) United States Patent
Masuda et al.

(10) Patent No.: US 6,296,621 B1
(45) Date of Patent: Oct. 2, 2001

(54) RECEPTACLE FOR PASSIVE DRUG DELIVERY

(75) Inventors: Kouichirou Masuda, Kashiwara; Kazumasa Maeda, Kadoma; Haruki Kazama, Musashino, all of (JP); Brian J. Gorman, Williams Bay, WI (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/702,377

(22) Filed: Aug. 23, 1996

(51) Int. Cl.$^7$ .................................................. A61M 37/00
(52) U.S. Cl. ............................ 604/89; 604/85; 604/91; 604/83; 604/248
(58) Field of Search ................................ 604/85, 91, 89, 604/411, 414, 905, 30, 32, 246, 247, 248; 222/83, 211, 479, 564, 108; 251/149.2, 210, 205, 304, 309, 310; 137/625.36, 625.39, 625.4, 625.46

(56) References Cited

U.S. PATENT DOCUMENTS

| | | | |
|---|---|---|---|
| 4,581,014 | * | 4/1986 | Millerd et al. . |
| 4,804,366 | * | 2/1989 | Zdeb et al. . |
| 4,832,690 | | 5/1989 | Kuu . |
| 4,850,978 | | 7/1989 | Dudar et al. . |
| 4,874,366 | | 10/1989 | Zdeb et al. . |
| 4,936,829 | | 6/1990 | Zdeb et al. . |
| 5,024,657 | | 6/1991 | Needham et al. . |
| 5,049,129 | | 9/1991 | Zdeb et al. . |
| 5,074,844 | | 12/1991 | Zdeb et al. . |
| 5,167,642 | | 12/1992 | Fowles . |
| 5,226,900 | | 7/1993 | Bancsi et al. . |
| 5,356,380 | | 10/1994 | Hoekwater et al. . |
| 5,385,547 | | 1/1995 | Wong et al. . |
| 5,429,614 | | 7/1995 | Fowles et al. . |
| 5,484,406 | | 1/1996 | Wong et al. . |
| 5,547,471 | | 8/1996 | Thompson et al. . |
| 5,549,569 | * | 8/1996 | Lynn et al. ............................ 604/191 |
| 5,674,193 | * | 10/1997 | Hayes .................................... 604/28 |

FOREIGN PATENT DOCUMENTS

| | | |
|---|---|---|
| 9501133 | 1/1995 | (WO) . |
| 9501196 | 1/1995 | (WO) . |

* cited by examiner

*Primary Examiner*—Sharon Kennedy
*Assistant Examiner*—Catherine Serke
(74) *Attorney, Agent, or Firm*—Mark J. Buonaiuto; Paul E. Schaafsma

(57) ABSTRACT

The present invention provides a receptacle used in a passive drug delivery system. The receptacle includes first flow path for supplying along a fluid conduit a medical liquid, second flow path for introducing the medical liquid into a container containing a beneficial agent, third flow path for delivering a mixed solution containing the medical liquid and agent, and a guide valve for controlling the flow path by closing or opening the flow path.

7 Claims, 4 Drawing Sheets

RECEPTACLE FOR PASSIVE DRUG DELIVERY

FIELD OF THE INVENTION

This invention relates to a receptacle for a passive drug delivery system used in conjunction with an administration set in which a beneficial agent is reconstituted through a medical liquid delivered to a patient.

BACKGROUND OF THE INVENTION

Administration sets for intravenously administering a liquid, generally called a transfusion liquid, and sometimes containing a dextrose solution, a solution of salt or water (hereinafter called a medical liquid) is widely used. In such a set a particular drug is frequently mixed with the medical liquid to be administered.

The administration set generally comprises a container containing a large volume of medical liquid, a cylindrical instillator, a flow rate control means, a fluid filter, means for removing air, an injection site for injecting additional drug mixture, fluid conduits for intermediate connection, and means for coupling inlet and outlet portions. Conventionally, when the administration set is used to supply a patient with a medical liquid mixed with a particular agent, if the agent is not liquid, it is first liquefied by using a diluent or other agents and then infused into the injection site so that the agent is mixed with the medical liquid.

This method, however, carries a risk of various kinds of contamination that are attributable to the requirements for the work of infusing a drug into the medical solution and preparatory operations therefor. Various countermeasures have been taken to avoid these risks, and to relive the medical workers from the work.

Representatives of such countermeasures are described in Japanese Patent Publication Nos. 5-60758 and 5-81271. The system taught by these publications comprises disposing a vial-like drug container in the middle of a fluid conduit for a medical liquid, and passing the medical liquid through the drug container to deliver a mixed solution containing the medical solution and drug. This type of system is referred to as a passive drug delivery system.

In that system a socket or a receptacle and a cartridge to be coupled therewith are provided. The drug container is attached to the cartridge so that, the inside space of the drug container is made to communicate with the flow path of the medical solution.

When this passive drug delivery system is used, once the drug container is docked into the cartridge, there is no chance for the drug in the container to be exposed to the air, and all the mixing operation is automatically carried out by the medical solution, so that very high safety can be secured, and so that the work of the operator can be saved.

However, although the delivery of the drug is carried out under strictly controlled conditions, there are cases in which the removal or renewal of the drug container is needed after the drug has been delivered. These requirements are not appropriately met by the well-known system mentioned above. In other words, once the passive drug delivery system has been established, the drug container cannot easily be removed. This is because the system is generally designed for the medical solution to pass through the container to form a portion of the flow path for the medical solution.

What would therefore be advantageous is to provide a receptacle for a passive drug delivery system which can be used without interruption even when a drug container is to be removed or replaced, or which can be used without a drug container when it is not needed.

SUMMARY OF THE INVENTION

In one aspect the receptacle of this invention comprises first flow path means for supplying a medical liquid along a fluid conduit, second flow path means for introducing the medical liquid into a container for a beneficial agent, third flow path means for delivering a mixed solution containing the medical liquid and agent, and a guide valve for controlling the flow path means by closing or opening the flow path.

In one embodiment of the receptacle of this invention, the flow path comprises a chamber inside the receptacle and a space formed around a cannula by a member to hold the cannula. The flow path comprises an opening to introduce the solution formed at the top of the cannula, the cannula, an opening for delivery formed at the bottom of the cannula, and a chamber inside the receptacle.

In another embodiment of the receptacle of this invention, the chamber inside the receptacle is divided into an upper chamber and a lower chamber. Both upper and lower chambers are further divided into a front chamber and a rear chamber. The upper rear chamber and the lower rear chamber serve for the introducing flow path and for the delivery flow path, respectively. A guide valve closes or opens communications between the upper front chamber and upper rear chamber and between the lower front chamber and the lower rear chamber, and at the same time the valve closes or opens communications between the upper front chamber and the lower front chamber, respectively.

In a further embodiment of the receptacle of this invention, a fixture for the drug container is disposed at the holding member so that a member for fixing the container is provided.

DETAILED DESCRIPTION OF THE PREFERRED EMBODIMENTS

Preferred embodiments of this invention will now be detailed by reference to the attached drawings.

FIGS. 1–4 exemplify a passive delivery system wherein a receptacle of made in accordance with the principles of the present invention is used.

Figure 1:
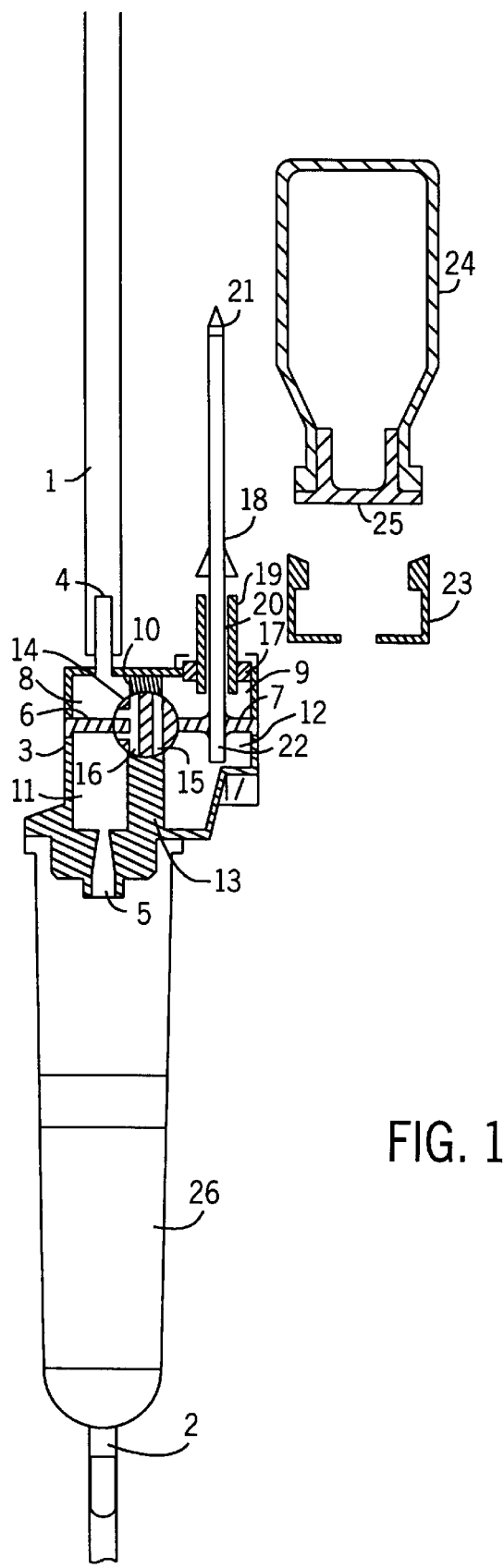
FIG. 1 is a partial sectional view exemplifying a receptacle made in accordance with the principles of the present invention used in a passive drug delivery system.

This invention, the components of which are shown in FIG. 1, comprises a receptacle or a socket 3, a drug container 24, and a fixing member 23. The receptacle 3, has mechanisms to introduce a medical liquid into the drug container, and passively deliver the solution containing the drug. That is, the receptacle constitutes a first flow path which directly guides the medical liquid to an outlet, a second flow path which introduces the medical liquid into the drug container, and a third flow path that delivers the mixed solution from the container, and a guide valve for controlling these flow paths.

Referring to FIG. 1, an inlet fluid conduit 1 is provided which is in communication with a parenteral container (not shown) containing the medical liquid. An outlet fluid conduit communicating with an intravenous injection needle to be connected to a patient's vein. The inlet and outlet fluid conduits 1 and 2 are not require to be directly connected with the medical liquid source and the injection needle, respectively. If necessary, for example, the conduit can be connected via flow rate control means, an injection site or the like. Although in FIG. 1 an air chamber 26 is disposed adjacent to the receptacle 3 between the conduits 1,2, the air chamber is not necessarily provided next to the receptacle 3. All components fundamentally communicate with each other by means of fluid conduits.

The receptacle 3 has an inlet 4 and an outlet 5 each of which is connected to the inlet conduit 1 and outlet conduit 2, respectively. Although the outlet 5 opens to the air chamber 26, and is connected to the outlet conduit 2, it can be directly connected to the outlet conduit 2 with no air chamber 26 in-between.

As already mentioned, the receptacle 3 serves to establish a first flow path which directly guides the medical liquid to the outlet 5, a second flow path which introduces the medical liquid into the drug container 24, and a third flow path that delivers the mixed solution from the drug container, and a guide valve 14 for controlling these flow paths.

Shown in the drawings as an example is a type of mechanism using a cannula 18, where through the medical liquid is introduced into the drug container 24, and the solution of an agent or drug in the medical liquid is passively delivered. However, this invention should not be limited to this mechanism.

In the structure of the drawings, the receptacle 3 is provided with a mount 17 for the cannula 18, on which mount a support 19 for the drug container is installed.

The support 19 for the drug container surrounds the cannula 18 so that an annular space 20 is formed there between. The cannula 18 is a hollow tube, and has an inlet opening 21 and an outlet opening 22 at its top and bottom, respectively.

The receptacle 3 has four chambers therein. That is, the inside of the receptacle 3, is divided into an upper chamber and a lower chamber by a front partition 6 and a rear partition 7. The upper chamber is further divided into a front upper chamber 8 and a rear upper chamber by an upper partition 10, and the lower chamber is divided into a front lower chamber 11 and a rear lower chamber 12 by a lower partition 13.

The front upper chamber 8 communicates with the receptacle inlet 4. The rear upper chamber 9 communicates with the lower end of the annular space 20, an inlet through which the medical solution is introduced into the drug container 20.

The outlet opening 22 of the cannula 18 opens to the rear lower chamber 12. The front lower chamber 11 communicates with the receptacle outlet 5.

The guide valve 14 has a lower path 15 and a front/upper path 16. The guide valve 14 is disposed in the receptacle 3 so as to control the flow of the medical liquid by closing and opening the flow paths. That is, the guide value 14 selectively closes the medical liquid supply flow path from the front upper chamber 8 to the front lower chamber 11 and at the same time opens the medical liquid introduction flow path from the front upper chamber 8 to the rear upper chamber 9 or it opens the medical liquid supply flow path and at the same time it closes the medical liquid introduction flow path.

When the medical liquid is guided into the rear upper chamber 9, after being introduced into the drug container 24, as is seen from the drawings, the mixed solution is delivered into the rear lower chamber 12, passed through the lower path of the guide valve 14 to the front lower chamber 11, and then supplied to a patient via the receptacle outlet 5.

The medical liquid is introduced into the drug container 24 via the annular space 20. The introduced medical liquid is mixed with an agent to form a mixed solution. The mixed solution is delivered into the rear lower chamber 12 through the inlet opening 21, the hollow part, and the outlet 22, of the cannula 18, and then the delivered solution is supplied to the patient via the lower path 1 5 of the guide valve 14.

The drug container 24 has a pierceable or sealing part 25, at which the container 24 is fixed by a fixture 23.

An agent is sealed within the drug container 24, the inlet of which forms a sealing part 25 constituted by a relatively breakable material. The cannula 18 is inserted into the drug container by being pierced through the sealing part along with the support 1 9 therefor. The annular space 20 is formed between the cannula and 18 and the support 19.

Figure 2:
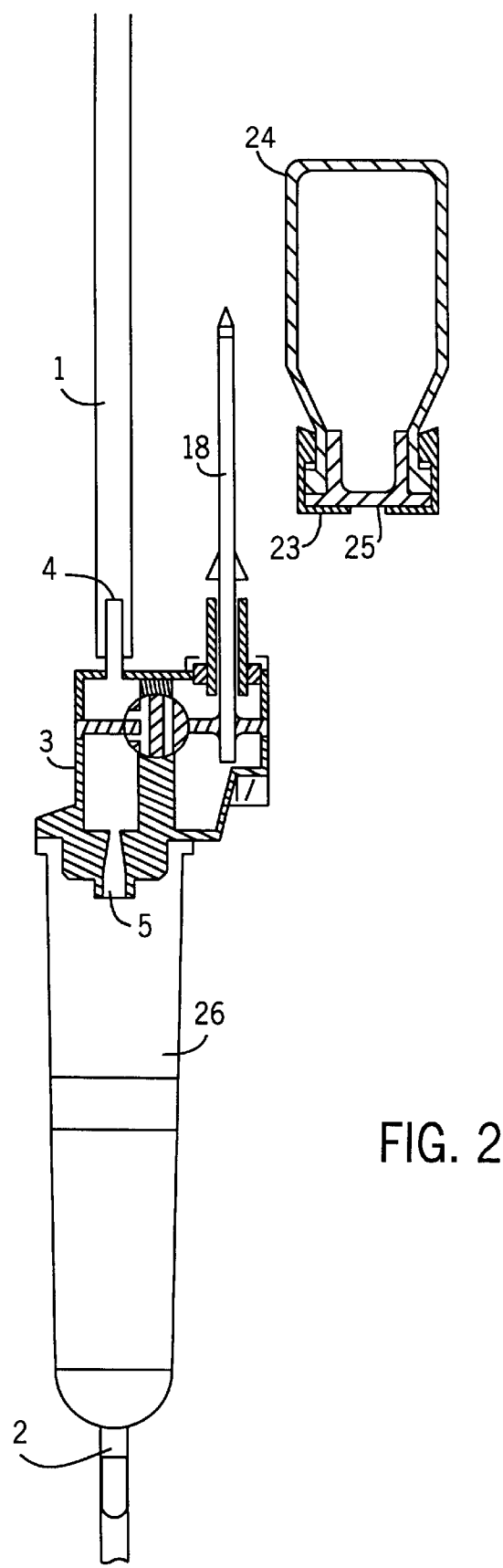
FIG. 2 is a partial sectional view exemplifying a mode of use of the receptacle of FIG. 1 used in a passive drug delivery system.
Figure 3:
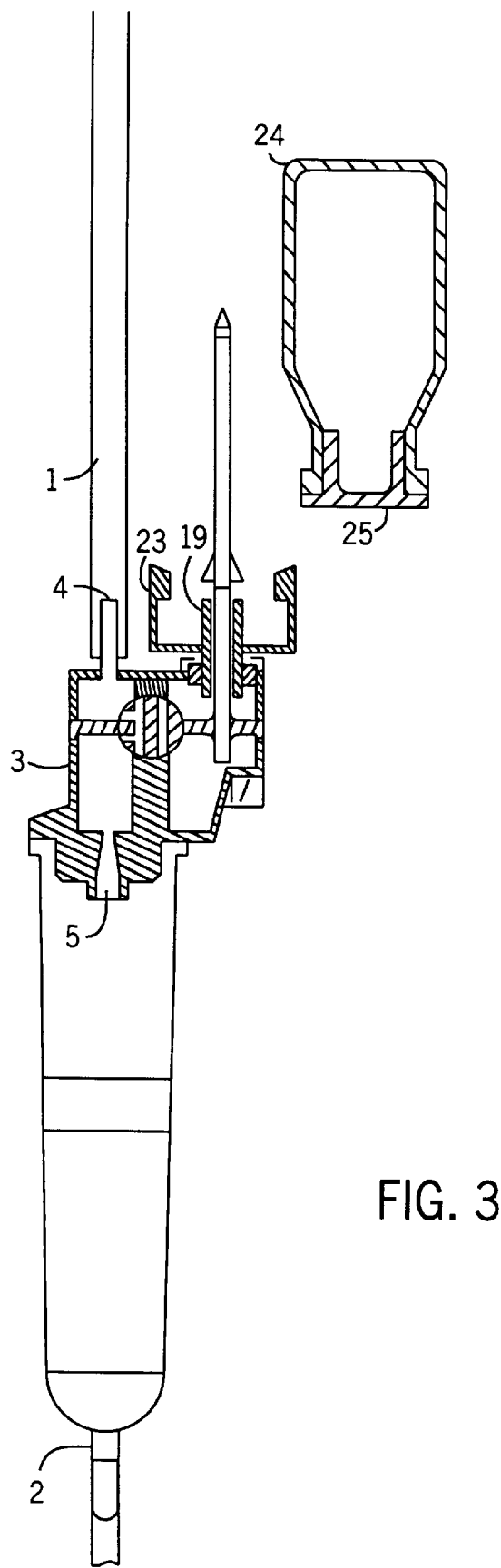
FIG. 3 is a partial sectional view exemplifying another mode of use of the receptacle of FIG. 2 used in a passive drug delivery system.

The fixing member 23 is used by being fixed to the drug container 24 or to the receptacle 3 in advance, as shown in FIGS. 2 and 3, respectively. In both cases, using the fixture 23 is advantageous in that it is applicable to any kind of drug containers.

Figure 4:
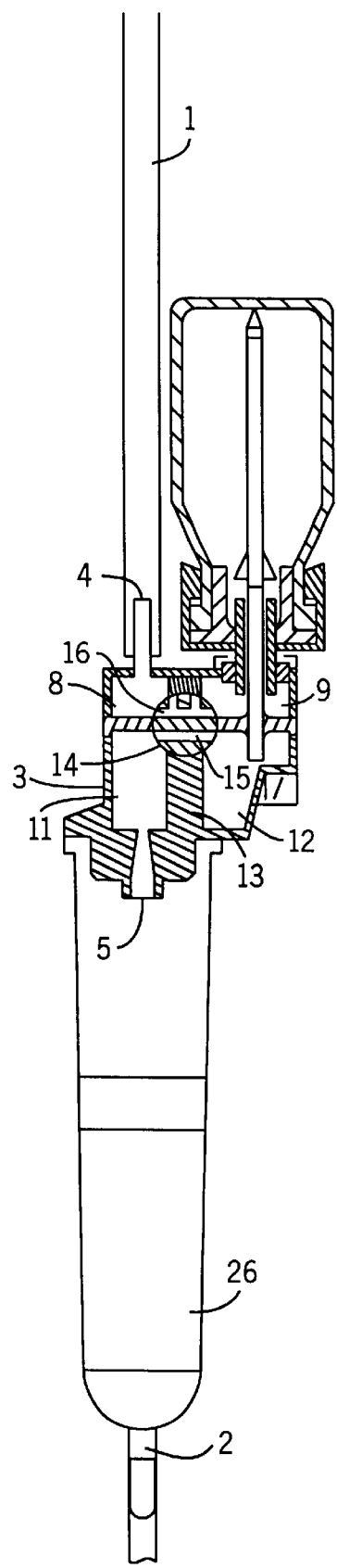
FIG. 4 is a partial sectional view exemplifying a state in use of the receptacle of FIG. 1 used in a passive drug delivery system.

FIG. 4 exemplifies the receptacle 3 in use of this invention. The guide valve 14 of FIG. 4 shows a state different from that of FIGS. 1–3, and the medical liquid is being introduced into the drug container 24.

That is, in FIGS. 1–3 the guide valve 14 closes the flow path between the front upper chamber 8 and the rear upper chamber 9, and at the same time the flow path between the front lower chamber 11 and the rear lower chamber 1 2 is also closed. On the other hand the flow path between the front upper chamber 8 and the front lower chamber 11 is opened by the front/upper path 1 6 of the guide valve 14.

If the medical liquid is supplied in this state, the medical liquid flows from the inlet 4 to the outlet 5 through the front upper chamber 8, the front upper path 16, and the front lower chamber 11. As the medical liquid is not thus supplied to the rear upper chamber 9, any mechanism connected to the rear upper chamber 9, including the medical liquid introduction flow path and the mixed solution delivery flow path, is closed so that all mechanisms are not influenced at all by the medical liquid, no matter what state they are in. This means that in this state the supply of the medical liquid can be carried out without being affected by the attachment or removal of the drug container. Thus, the fixing, exchange, and the like of the drug container can be freely accomplished without affecting the instillation operation. In other words, the supply of the medical solution can be continued regardless of whether the drug container is present, and there is no possibility of causing any difficulty such as leakages.

The state shown in FIG. 4 differs from those shown in FIGS. 1–3. In FIG. 4 the front and rear chambers and each of the mechanisms communicate through the guide valve 14, while the flow path from the upper chamber to the lower chamber is closed. In this state, the medical liquid passes from the receptacle inlet 4 through the front/upper chamber 8 and the front/upper path 1 6 of the guide valve to the rear upper chamber 9. Since in the rear upper chamber the medical liquid introduction flow path, which guides the medical liquid into the drug container, is provided, the introduced medical liquid is mixed with the drug therein.

As the cannula 18 is attached through the support 19 to the mount 17 disposed at the rear upper chamber 9, the medical liquid is introduced through the annular space formed between the cannula and the support 19 into the drug container 24. The mixed solution passes from the inlet opening 21 of the cannula 18 through the inside hollow and the outlet opening 22 of the cannula to the lower chamber.

The front and rear chambers of the lower chamber of FIG. 4, divided by the partition 13, communicate through the lower path 15 of the guide valve 14. Thus, the mixed solution of the drug in the medical solution flows from the rear lower chamber 12 through the lower path 15 of the valve to the front lower chamber 11 to be delivered from the outlet 5. The passive drug delivery system can function only in the state shown in FIG. 4.

Since the passive drug delivery system using the receptacle of the invention functions as stated above, the receptacle can be used by being inserted between the flow path of the medical liquid without the drug container being present. In case of need, the system can perform its function as a passive drug delivery system by attaching the drug container thereto, and by operating the guide valve. After the completion of the drug delivery or at the exchange of the drug container, the system can be continuously used in the same state as it has been used by reoperating the valve, and by removing the drug container.

Although this invention was explained by reference to the attached drawings, the receptacle of this invention used in the passive drug delivery system is not limited to those used in the embodiments recited. Although the explanation was directed to the system wherein, for example, a cannula is provided in the rear upper chamber, two cannulas, large and small ones, can also be provided in the rear upper chamber as a mechanism for supplying the medical liquid to the drug container and for passively delivering the solution of the drug in the medical liquid. That is, the bottom and top openings of the small cannula may be opened to the rear upper chamber and the outside of the receptacle respectively, and the top and the bottom openings of the large cannula may be opened above the top of the small cannula and the inside of the lower chamber, respectively. In this case, the system can perform the same function as that of the passive drug delivery system shown in the drawings. Further, the shape of the guide valve is not limited to that shown in the drawings. Any shape of a valve can be used provided it can perform the same function.

Although the receptacle of this invention is used in a passive drug delivery system, the drug container can be freely attached or removed while the medical liquid is continuously fed. That is, the present invention provided a passive drug delivery system which, as needed, permits the removal of the drug container without affecting the flow of the medical liquid through the system, ensuring that the usefulness of the system is enhanced.

It should be understood that various changes and modifications preferred in to the embodiment described herein will be apparent to those skilled in the art. Such changes and modifications can be made without departing from the spirit and scope of the present invention and without demising its attendance advantages. It is therefore intended that such changes and modifications be covered by the appended claims.

What is claimed is:

1. A device disposed in a fluid conduit for supplying a medical liquid comprising:

a receptacle adapted to receive an apparatus to deliver a passively reconstituted beneficial agent to a patient;

a first flow path adapted to supply the medical liquid along the fluid conduit;

an upper chamber inside the receptacle and a space formed around a cannula by a member to hold the cannula, the upper chamber adapted to introduce the medical liquid into a container containing the beneficial agent, wherein the medical liquid and the beneficial agent from a mixed solution;

an opening to introduce the solution formed at the top of the cannula, an opening for delivery formed at the bottom of the cannula, and a lower chamber inside the receptacle wherein the mixed solution is delivered;

the mixed solution is delivered;

a guide valve means located between the first flow path and the second flow path for controlling the flow paths by closing or opening communication between the first flow path and the second flow path;

a cannula extending from the third chamber into the apparatus to deliver the passively reconstituted beneficial agent to a patient; and a space formed around the cannula extending from and in fluid communication with the second chamber into the apparatus to deliver the passively reconstituted beneficial agent to a patient.

2. The device of claim 1, wherein wherein both the upper and lower chambers are further divided into a front chamber and a rear chamber so that the upper rear chamber and the lower rear chamber serve for the second flow path means and for the third flow path means, respectively, and wherein the guide valve closes or opens communications between the upper front and upper rear chamber, and the valve closes or opens communications between the upper front chamber and the lower front chamber, respectively.

3. The device of claim 2, wherein a fixing member for the container is disposed at a mount on the second flow path means.

4. The device of claim 1, wherein a fixing member for the container is disposed at a mount on the second flow path means.

5. The device of claim 1 wherein a fixing member for the container is disposed at a mount on the second chamber.

6. A receptacle disposed in a fluid conduit for supplying a medical liquid, the receptacle adapted to receive an apparatus to deliver a passively reconstituted beneficial agent to a patient, the receptacle comprising:

a first chamber in communication with an inlet;

a second chamber in communication with the apparatus to deliver a passively reconstituted beneficial agent to a patient;

a third chamber in downstream communication with the apparatus to deliver a passively reconstituted beneficial agent to a patient;

a fourth chamber in communication with an outlet;

guide valve means for establishing communication between the first chamber and the fourth chamber while closing communication between the second chamber and the third chamber;

the guide valve means further being for establishing communication between the first chamber and the second chamber while establishing communication between the third chamber and the fourth chamber;

a cannula extending from the third chamber into the apparatus to deliver the passively reconstituted beneficial agent to a patient; and a space formed around the cannula extending from and in fluid communication with the second chamber into the apparatus to deliver the passively reconstituted beneficial agent to a patient.

7. The receptacle of claim 6 wherein a fixing member for the container is disposed at a mount on the second chamber.

* * * * *

UNITED STATES PATENT AND TRADEMARK OFFICE
CERTIFICATE OF CORRECTION

PATENT NO. : 6,296,621 B1  
DATED : October 2, 2001  
INVENTOR(S) : Masuda et al.

Page 1 of 1

It is certified that error appears in the above-identified patent and that said Letters Patent is hereby corrected as shown below:

<u>Column 6,</u>  
Line 2, the word "from" should be replaced with -- form --.

Signed and Sealed this

Thirtieth Day of April, 2002

*Attest:*

*Attesting Officer*

JAMES E. ROGAN  
*Director of the United States Patent and Trademark Office*